United States Patent [19]

Suzuki et al.

[11] Patent Number: 4,525,229
[45] Date of Patent: Jun. 25, 1985

[54] METHOD FOR ATTACHING ELASTIC BAND TO SANITARY ARTICLES

[75] Inventors: Migaku Suzuki, Kawanoe; Mitsuzo Ochi; Satoshi Nozaki, both of Ehime, all of Japan

[73] Assignee: UniCharm Corporation, Ehime, Japan

[21] Appl. No.: 561,479

[22] Filed: Dec. 14, 1983

[30] Foreign Application Priority Data

Dec. 15, 1982 [JP] Japan ................ 57-219833

[51] Int. Cl.³ .............. B32B 31/08; B32B 31/18; A61F 13/16
[52] U.S. Cl. .................. 156/161; 156/164; 156/176; 156/229; 156/264; 156/301
[58] Field of Search .......... 156/160, 161, 164, 16 B, 156/229, 285, 297, 301, 302, 269, 264, 176, 494, 495, 519

[56] References Cited

U.S. PATENT DOCUMENTS

| | | | |
|---|---|---|---|
| 3,963,557 | 6/1976 | Patterson | 156/519 |
| 4,081,301 | 3/1978 | Buell | 156/301 |
| 4,285,747 | 8/1981 | Rega | 156/164 |
| 4,364,787 | 12/1982 | Radzins | 156/164 |
| 4,397,704 | 8/1983 | Frick | 156/285 |
| 4,413,623 | 11/1983 | Pieniak | 156/160 |

Primary Examiner—Michael Ball
Attorney, Agent, or Firm—Fred Philpitt

[57] ABSTRACT

Here is disclosed method for attaching elastic band to sanitary articles such as disposable diapers. The elastic band is cut into predetermined lengths which are then intermittently attached by adhesive to a web forming said articles. Said elastic band is severed on a surface of a rotary suction drum so that the respective lengths thus severed and isolated may be intermittently attached to said web. Said elastic band may comprise a plurality of relatively narrow or fine rubber strands. Particularly in such a case, said elastic band is attached to a support tape wider than said elastic band and having high flexibility before cutting so that these rubber strands may be reliably held on the surface of said suction drum.

9 Claims, 13 Drawing Figures

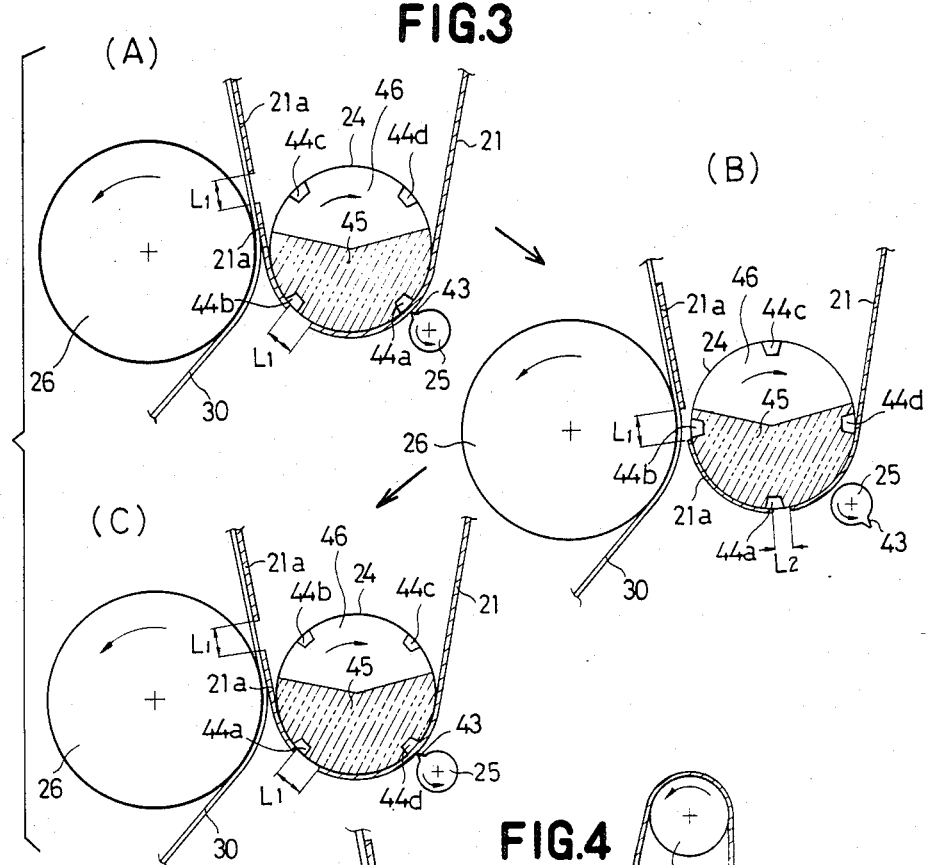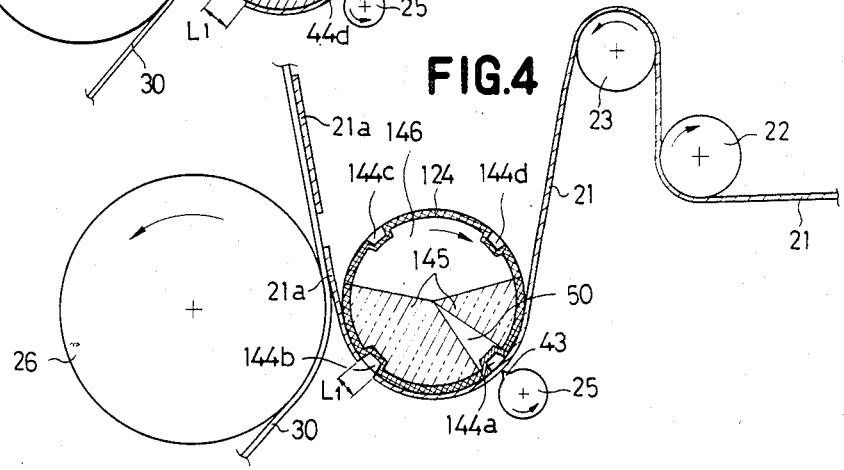

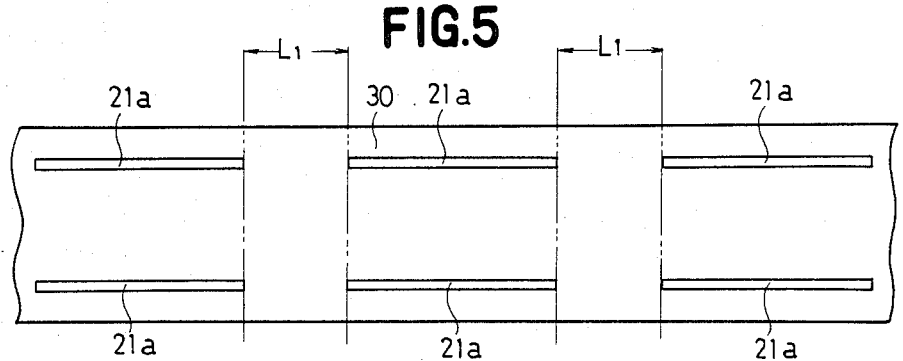
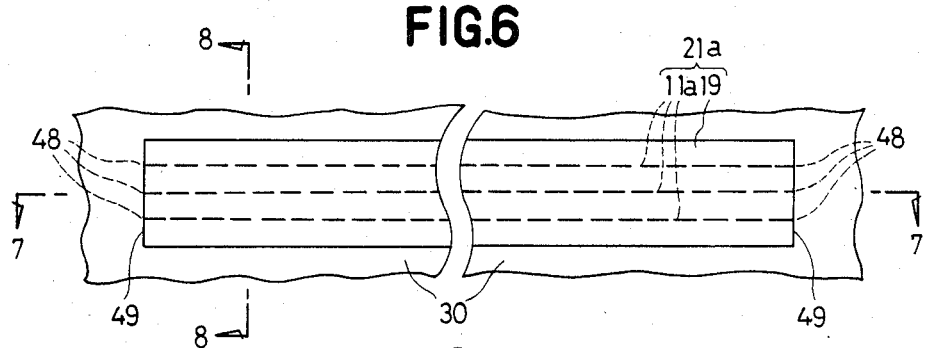
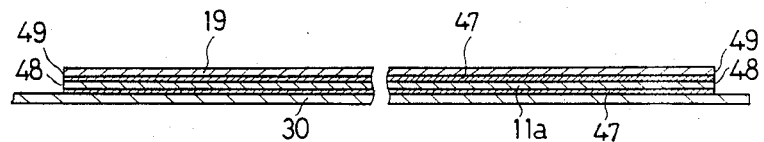
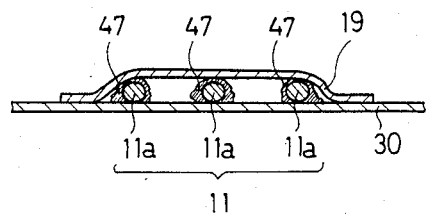

METHOD FOR ATTACHING ELASTIC BAND TO SANITARY ARTICLES

BACKGROUND OF THE INVENTION

The method for intermittently attaching elastic band to a continuously moving web in a stretched condition in manufacture of absorbent articles such as disposable diaper has already been disclosed, for example, by the specification of U.S. Pat. No. 4,081,301. According to the method of this patent, the continuous elastic band having adhesive intermittently applied thereon is attached to the web forming interconnected diapers and then said elastic band is cut transversely in areas which have no adhesive applied thereon simultaneously with individual articles from said web, allowing the severed, unadhered ends of said elastic band to relax and contract to their unstretched state so that said elastic band may be attached to the individual diapers only in the areas destined to surround legs of the user. However, this method of prior art is disadvantageous in that the finished diaper will have unsealed arears at opposite ends so as to allow the unsealed portions of the elastic band to contract and thereby a urine leakage may occur through these unsealed arears. Further, the elastic band attached to said web is transported in continuous state over a relatively long distance from the initial step of attaching said elastic band to said web towards the final step of cutting said elastic band together with said web with adhesive applied on said elastic band remaining still not set, so that the elastic band may be sometimes displaced transversely of said web in the course of transport thereof and finally prevented from being properly attached to the web at a predetermined position. Such a problem is not negligible particularly when said elastic band is replaced by a plurality of fine rubber strands which are arranged in parallel to one another at given intervals to be attached to said web.

OBJECTS OF THE INVENTION

An object of the present invention is, in view of such disadvantages as mentioned above, to provide a method so improved that a continuous elastic band having adhesive applied thereon is previously cut into predetermined lengths and these lengths of the elastic band are intermittently attached to a continuously moving web forming interconnected articles.

Another object of the present invention is to provide a method so improved that the continuously moving web to which the lastic band cut into said predetermined lengths has been intermittently attached may be severed in the areas where said elastic band is not present notly to obtain the individual articles but also to seal the severed ends of said articles.

Further object of the present invention is to provide a method so improved that the elastic band previously cut into predetermined lengths is attached to the web in the initial step of manufacture of the articles, as has previously been described, and thereby said elastic band may be surely kept against a displacement transverse of said web or a separation therefrom.

The other objects of the present invention will be apparent from a following description of the invention more in detail.

SUMMARY OF THE INVENTION

According to the present invention, the above mentioned objects are achieved by a method for intermittently attaching an elastic band, in a stretched condition, with adhesive, to a continuously moving web forming interconnected articles such as sanitary articles on each side thereof longitudinally at predetermined intervals, said method comprising steps of: continuously or intermittently applying adhesive on the continuously moving elastic band in a stretched condition; superposing said elastic band on a continuously moving support tape having a sufficiently high flexibility not to hinder a given expansion and contraction ability of said elastic band and a width larger than that of said elastic band and then nipping such assembly between a first pair of nip rollers to form a combined elastic band; continuously feeding said combined elastic band onto a surface of a rotary suction drum and severing said combined elastic band by a cutter adapted to be opposed to the surface of said suction drum when the latter has rotated by a predetermined angle; intermittently feeding said combined elastic band which has been severed and isolated on the surface of said suction drum into the predetermined lengths onto each side and longitudinally of the web being continuously fed around a second nip roller placed to be opposed to said suction drum so as to form the interconnected articles; and severing said web transversely of said web in the areas defined between the longitudinal ends of the respectively adjacent lengths of the severed combined elastic band attached to said web to form the individual articles. In a particularly preferred embodiment, the combined elastic band is severed on the surface of the rotary suction drum into predetermined lengths which are automatically spaced from one another at a distance at which these lengths of the combined elastic band are to be intermittently attached to the web. The present invention will find its most preferred application in so-called disposable diaper, although the present invention is never limited to this field of application.

BRIEF DESCRIPTION OF THE INVENTION

Figure 2:
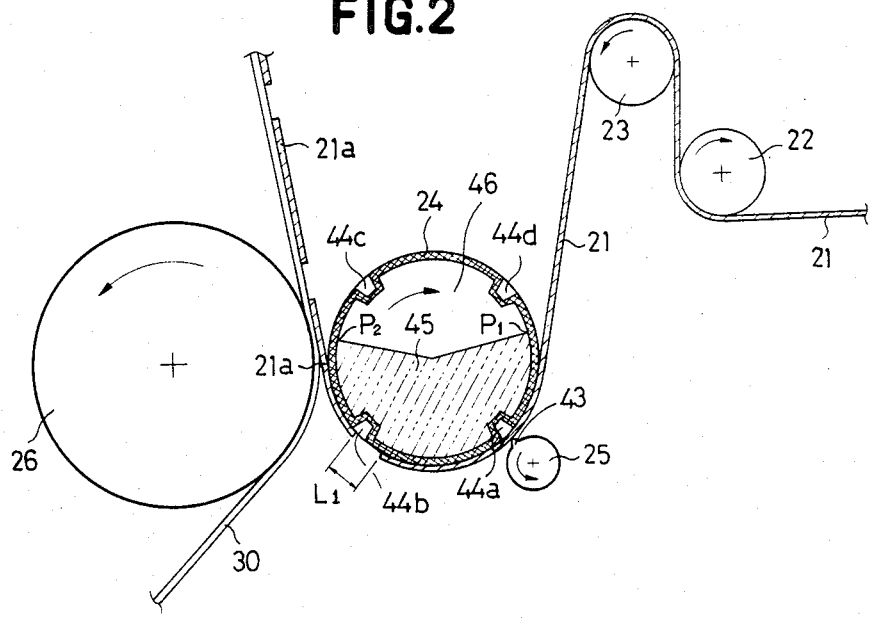
FIG. 2 is a schematic side view of a part enclosed by a chain line in FIG. 1, illustrating steps of severing the combined elastic band and attaching said band to the web, in enlarged scale.
Figure 9:
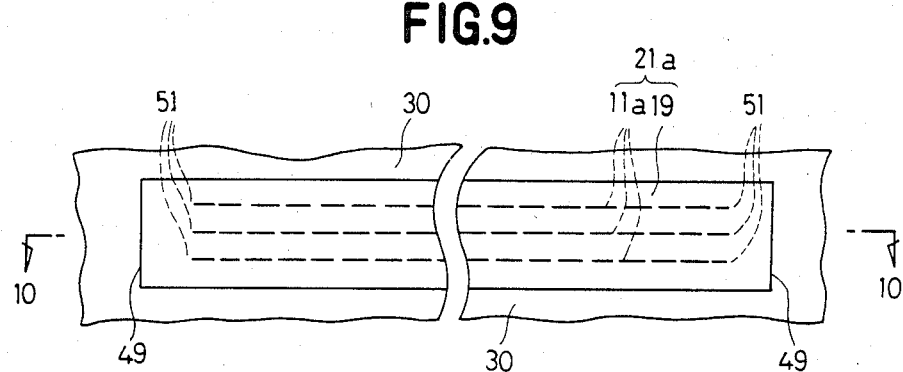
Figure 10:
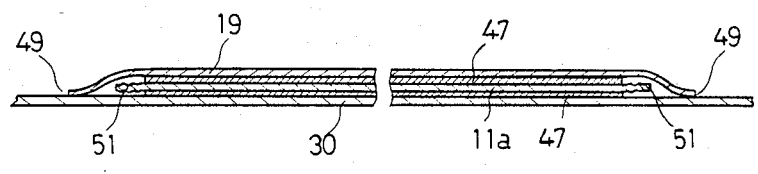

FIGS. 3(A), (B) and (C) are schematic side views separately illustrating successive operation of the combined elastic band in FIG. 2;

FIG. 4 is a schematic side view illustrating steps corresponding to those as illustrated by FIG. 2 but with a rotary suction drum partially different from that employed in the step as illustrated by FIG. 2;

FIG. 5 is a fragmentary plan view illustrating a state in which the combined elastic band has intermittently been attached to the web;

FIG. 6 is an enlarged fragmentary plan view corresponding to FIG. 5;

FIG. 7 is an enlarged sectional view taken along a line 7—7 in FIG. 6;

FIG. 8 is an enlarged sectional view taken along a line 8—8 in FIG. 6;

FIG. 9 is a fragmentary plan view illustrating a state different from that as illustrated by FIG. 6, in which the combined elastic band has been attached to the web;

FIG. 10 is an enlarged sectional view taken along a line 10—10 in FIG. 9; and

Figure 11:
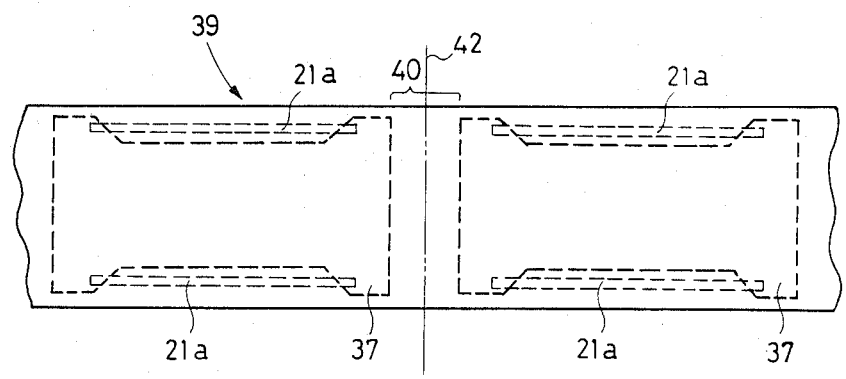

FIG. 11 is a fragmentary plan view illustrating interconnected diapers.

DETAILED DESCRIPTION OF THE INVENTION

Figure 1:
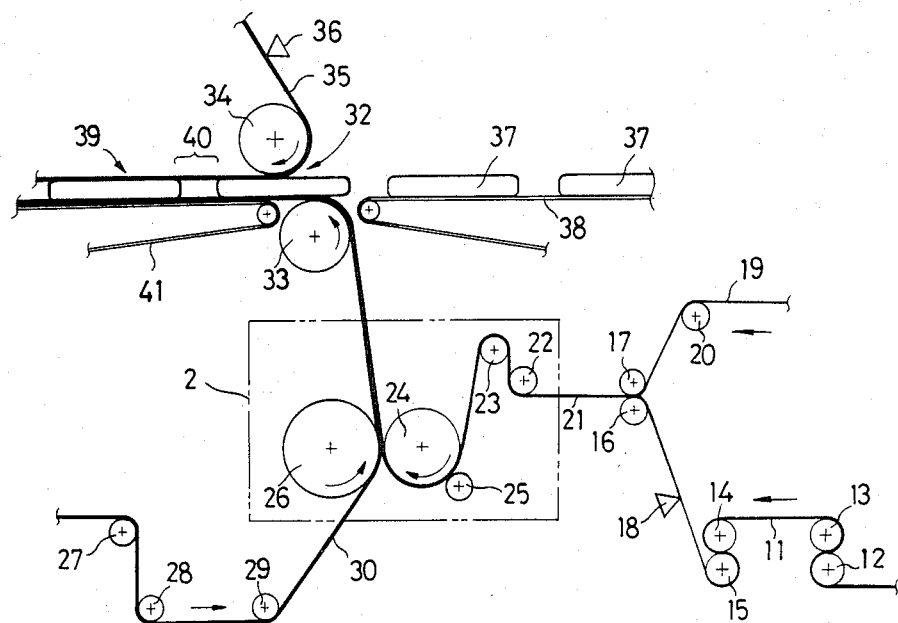
FIG. 1 is a side view schematically illustrating a process for attaching an elastic band to disposable diapers as one embodiment of the method according to the present invention.

Referring to FIG. 1, a continuous elastic band 11 is continuously fed through pairs of draft rollers 12, 13; 14, 15 to a pair of nip rollers 16, 17. A circumferential velocity of the pair of draft rollers 14, 15 is adjusted higher than that of the pair of draft rollers 12, 13 so that the elastic band 11 may be stretched at a predetermined ratio. An applicator 18 continuously or intermittently applies on the elastic band 11 hot-melt adhesive having an elasticity. Meanwhile, a continuous support tape 19 of material such as plastic film or nonwoven fabric having a flexibility sufficiently high not to hinder a predetermined expansion and contraction ability of the elastic band 11 and a width of 10 to 70 mm, preferably 20 to 40 mm is continuously fed through a guide roller 20 to the pair of nip rollers 16, 17 under a predetermined tension. In consequence, the elastic band 11 is attached to the support tape integrally therewith in a stretched condition between the pair of nip rollers 16, 17. A primary purpose of attaching the elastic band to the support tape 19 is to assure that said elastic band can be reliably held on a suction drum which will be described more in detail later even when said elastic band has a relative narrow width. It should be noted here that an assembly of the elastic band 11 thus attached to the support tape 19 will be referred to hereinafter as a combined elastic band 21. This combined elastic band 21 is continuously fed through a pair of tension rollers 22, 23 onto a peripheral surface of a rotary suction drum 24. To said surface of the suction drum 24 opposed a rotary cutter 25 adapted to be synchronously operated every time said drum has rotated by a predetermined angle. A circumferential velocity of the suction drum 24 is set to a level higher than that at which the combined elastic band 21 is fed from the pair of tension rollers 22, 23 so that the combined elastic band 21 is severed into predetermined lengths on the surface of the suction drum 24 and simultaneously these severed lengths are automatically spaced from one another at predetermined intervals (this aspect will be described in detail later). The combined elastic band 21 thus severed and spaced from one another is intermittently attached with interposition of said adhesive applied on the elastic band 11 to a continuous web 30 which is continuously fed through guide rollers 27, 28, 29 to a nip roller 26 placed to face the surface of said suction drum 24 and the same circumferential velocity as that of said drum, at said predetermined intervals. Such operation of attaching the combined elastic band 21 to the web 30 is actually performed on both sides of said web and longitudinally of said web (as seen in FIGS. 5 and 11), but the attaching operation will be described with respect only to one side of the web to simplify the description. The web 30 is made of plastic film or like destined to be ultimately formed into a water-impervious backsheet. This web 30 is fed to a pair of nip rollers 33, 34 having the same circumferential velocity as those of the suction drum 24 as well as of the nip roller 26 both placed to face an assembly station 32 while maintained in a predetermined tension. On one hand, a continuous web 35 of nonwoven fabric or like destined to be ultimate formed into a water-pervious topsheet and having hotmelt adhesive previously applied thereon from an applicator 36 for attaching said web 35 to an absorbent core of the diaper and/or the continuous web 30 is fed to the assembly station 32 while maintained in a predetermined tension. On the other hand, the absorbent cores 37 prefabricated of fluffy pulp or like are fed at predetermined intervals to said assembly station 32 by a belt conveyor 38 having the same linear velocity as those of the webs 30, 35. Thus the respective absorbent cores 37 are interposed between the webs 30, 35 at predetermined intervals and these components are bonded in unison at this assembly station 32. It is obvious in this step that the respective absorbent cores 37 should be fed in a positional alignment with the associated lengths of said combined elastic band 21 attached to the web 30 on each side. Interconnected diapers 39 thus assembled are fed by a belt conveyor 41 to a following severance station (not shown) in which said interconnected diapers 39 are severed along transversely middle line (as indicated by a chain line 42 in FIG. 11) in intermediate areas 40 where said respective absorbent cores 37 are not present into individual diapers. Already in the step of severance, there is no end of said elastic band 11 left to contract, so that the webs 30, 35 can be sealed to each other along the whole lengths thereof. Such sealing effect may be achieved, for example, either by heat seal occurring simultaneously with the severance or by previously applying adhesive on the inner surfaces of the respective webs 30, 35 in the areas adjacent the respective severance lines and exerting a pressure to these adhered areas while these webs 30, 35 are severed.

It is preferred to provide said draft roller 16 and said tension roller 23 on their peripheral surfaces with suitable means to prevent adhesive applied on said elastic band 11 from cling to said peripheral surfaces, for example, to coat said peripheral surfaces with mold release agent such as silicon film, since said adhesive on said elastic band 11 is inevitably brought into contact with said peripheral surfaces. Said rollers 22, 23 may be draft rollers. Furthermore, it is preferred that said rollers 16, 23 are chilling rollers in which cooling water is circulated.

Said elastic band 11 preferably comprises a plurality of fine rubber strands each having a relatively low tensile stress. In the event such plurality of rubber strands are employed in the method according to the present invention, however, it is preferred to provide between said pairs of draft rollers 14, 15 and nip rollers 16, 17 a suitable means assuring said respective fine rubber strands to be maintained at predetermined spacings from one another transversely of said support tape 19 when attached to this support tape 19, or to interpose between said respective pairs of rollers a separate roller provided on its peripheral surface with guide grooves for said respective rubber strands at predetermined intervals longitudinally of said peripheral surface. When said plurality of rubber strands are employed, it is also preferred that these individual rubber strands are provisionarily bonded together as lightly as easily separable, then separated by a suitable separating means from one another under a stretching treatment and thereafter applied with adhesive to equate stretches of the respective rubber strands. Means and measures to achieve this are disclosed in the specification of European patent application No. 83103636.3 filed in the name of the applicant of the present application and such disclosure is quoted here for reference, when it is considered necessary.

FIG. 2 illustrates by way of example the suction drum 24 and feeding of said combined elastic band 21 to this suction drum. According to this embodiment, the rotary suction drum 24 is defined by a porous peripheral wall carrying on its outer surface counter knives 44a, 44b, 44c, 44d cooperating with an edge 43 of the rotary cutter 25 and has within said peripheral wall a stationary suction zone 45 and a stationary non-suction zone 46 both always held at their predetermined positions as shown. It is important that the suction zone 45 extends in between a position $P_1$ appropriately spaced in a direction opposite to rotation of the suction drum 24 from a position of the cutter 25 at which the combined elastic band 21 is severed to a position $P_2$ adjacent a position at which the surfaces of said drum and the draft roller 26 are closest to each other. As previously described, the suction drum 24 has its circumferential velocity is set to a level higher than the velocity at which the combined elastic band 21 is fed from the tension rollers 22, 23 and the suction zone 45 provides an effective force always maintained at a sufficient level to hold the combined elastic band 21 onto the surface of said suction zone 45 even with a slippage of said combined elastic band 21 along said surface. The respective pairs of adjacent counter knives 44a, 44b, 44c, 44d pairly have center-distances larger than the predetermined lengths into which the combined elastic band 21 is severed. The suction drum 24 and the cutter 25 are so controlled that the edge 43 and the counter knives 44a, 44b, 44c, 44d are synchronously opposed to each other. Accordingly, the combined elastic band 21 is cut by the edge 43 of the cutter 24 on the surface of the drum associated with the suction zone 45 and a new leading end of the combined elastic band 21 formed every time said combined elastic band has been severed slips along said surface associated with the suction zone 45 against the effect of this zone while maintained in a tension on said surface. A severed and isolated length of the combined elastic band 21a is fixedly held on said surface in a tension under said effect and moved together with said surface, resulting in that the trailling end of the isolated band 21 is spaced from the new leading end of the remaining band 21 by a predetermined distance $L_1$. FIGS. 3(A), (B) and (C) illustrates a process in which this predetermined distance $L_1$ occurs. Specifically, FIG. 3(A) illustrates a state at a moment when the combined elastic band 21 is cut by the edge 43 of the cutter 25 in cooperation with the counter knife 44a; FIG. 3(B) illustrates a state in which the suction drum 21 has rotated by a certain angle and a distance $L_2$ from the new leading end of the combined elastic band 21 formed after every severance to the trailing end of the severed and isolated length of the combined elastic band 21a is being progressively enlarged to said predetermined distance $L_1$; and FIG. 3(C) illustrates a state at a moment when said distance $L_2$ has been enlarged just to said predetermined value $L_1$ and now said remaining combined elastic band 21 is going to be cut by the edge 43 of the cutter 25 in cooperation with the counter knife 44a behind said new leading end thereof. Each length 21a thus severed and isolated from the remaining combined elastic band 21 is fed with its leading end ahead, as said length 21a moves together with the drum surface into the non-suction zone 46, onto the continuously moving web 30 and intermittently attached by said adhesive applied on said elastic band 11 to said web 30 (see FIG. 5).

FIG. 4 illustrates another embodiment of said suction drum 24 itself and feeding said combined elastic band 21 to said suction drum 24. In this embodiment, the velocity at which the combined elastic band 21 is fed by the tension rollers 22, 23 corresponds to the circumferential velocity of the rotary suction drum 124. This suction drum 124 has the stationary suction zone 145 and the stationary non-suction zone 146 as in the previous embodiment of FIG. 2, but the suction drum 124 is distinguished from the suction drum 24 in that the former additionally has a second stationary non-suction zone 50. A portion of the drum surface associated with the second non-suction zone 50 has a span substantially corresponding to the intervals at which the respective lengths 21a severed and isolated from the combined elastic band 21 are intermittently attached to the web 30. Thus, the leading end of the combined elastic band 21 travels together with the drum surface while fixedly held onto the surface portion associated with the suction zone 145 across the non-suction zone 50. At the same time, the trailing end of the length 21a severed and isolated from the remaining combined elastic band 21 is spaced from the new leading end of said remaining combined elastic band 21 formed after every severance by a distance substantially equal to said distance $L_1$ as said leading end and said trailing end (or the leading end of said elastic band 11 and the trailing end of said support tape 19) contract in the event said adhesive has continuously been applied on said elastic band 11 of the combined elastic band 21 (21a) and as the leading end and the trailing end only of the elastic band 11 contract in the event said adhesive has been intermittently applied on said elastic band 11 so that the latter is severed in the areas where no adhesive has been applied at all.

FIGS. 5 through 10 illustrate a manner in which said lengths 21a severed and isolated from the remaining combined elastic band 21 have been attached to the web 30 and three fine rubber strands 11a are employed as said elastic band 11. The respective rubber strands 11a are attached by elastic hot-melt adhesive 47 applied completely around these respective rubber strands to said support tape 19 at predetermined intervals transversely of said support tape 19.

FIGS. 5 through 8 further illustrate a state in which said adhesive 47 has been continuously applied along a full length of each rubber strand 11a and severed ends 48 of the rubber strands 11a are aligned with the corresponding severed ends 49 of the support tape 19 when these both components have been attached to each other.

FIGS. 9 and 10 illustrate also a state in which the respective rubber strands 11a having said adhesive 47 intermittently applied therealong have been cut in areas 51 where no adhesive has been applied and, in consequence, these non-adhered areas have been retracted with respect to the severed ends 49 of the support tape 19.

It is preferred to use, as said respective rubber strands 11a, those having a unit cross-sectional area of 0.03 to 0.6 mm$^2$ per strand and total cross-sectional area of 0.12 to 2.7 mm$^2$ at a state corresponding to an elongation percentage of 100 to 400%. As said elastic hot-melt adhesive 47, pressure-sensitive adhesive of room temperature setting type is one of the preferables.

Said adhesive 47 is cooled in a course after said combined elastic band 21 (21a) has been nipped by the draft rollers 16, 17 and before said combined elastic band 21 (21a) is cut by the cutter 25 to a temperature at which a desired room temperature setting property is exhibited. Particularly when said elastic band 11 comprises said plurality of rubber strands 11a, the individual rubber strand has a relatively low tensile stress. As a result, said elastic band 11 remains attached to said support tape 19 with a high stability and there is no danger that said elastic band 11 might contract on said support tape or might be separated therefrom even after said elastic band 11 has been cut by the cutter 25 together with said support tape 19. Furthermore, said combined elastic bands 21a intermittently attached to said web 30 also remain attached to said web with a high stability at least in the course before movement to said draft roller 26, since said adhesive 47 is spread over said support tape 19 under a pressure in said course and thereby said support tape is also attached to said web 30.

Although the present invention has been described hereinabove in reference with the disposable diaper, it is obvious that the method according to the present invention is not limited to such application but may be usefully applied to the sanitary articles having the similar constructions such as a cover for the disposable diaper.

EXAMPLE

The disposable diaper was manufactured by following the steps as illustrated by FIGS. 1 and 2.

Four natural rubber strands welded together in parallel to one another, each strand having a diameter of 0.28 mm, the assembly thus welded together having a cross-sectional area of 0.123 mm$^2$ and weighing 0.13 g/mm, were stretched by 400% through a draft roller so that each strand has a tensile stress of 30 g. After these rubber strands had been continuously coated therearound with hot-melt pressure-sensitive adhesive sprayed through a slot nozzle means by an amount of 0.1 g/m per strand (at a temperature of 165° C.), these rubber strands were placed in said stretched state on polyethylene film having a width of 30 mm and a thickness of 7μ, obtained by the moderate or lower pressure process, at 4 mm intervals and then fed to a draft roller to form a combined elastic band. This combined elastic band was continuously fed to a rotary suction drum maintained at a suction force of 1500 mmAq and a suction capacity of 4 m$^3$/min, on which said combined elastic band was successively cut into lengths of 300 mm. The severed and isolated portions of the combined elastic band were intermittently fed onto a backsheet of polyethylene film having a thickness of 30μ obtained by a high pressure process so that both components may be attached to each other under a nipping effect of a draft roller opposed to suction drum. Thereafter the procedure as previously described in reference with FIG. 1 was followed to a diaper.

It was found that said combined elastic band (rubber strands) had been reliably and regularly placed in the diaper. It was observed also that said combined elastic band presents no hindrance during the step of feeding this to said backsheet as well as during the following steps.

As said adhesive, the commercially available one supplied from KANEBO N.S.C. (Co., Ltd.), Japan under a tradename "DUROTAC" and an article No. "MQ978" was used. This is a room temperature adhesive composed of elastomer (30 parts by weight), adhesive resin (60 parts by weight) and curing agent (10 parts by weight) as basic materials and a property of 38,000±7,000 cps at a temperature of 140° C. or 17,000±3,000 cps at a temperature of 160° C.

What is claimed is:

1. Method for intermittently attaching an elastic band, in a stretched condition, with adhesive, to a continuously moving web forming interconnected articles such as sanitary articles on each side thereof longitudinally at predetermined intervals, said method comprising steps of:
    (a) continuously or intermittently applying adhesive on the continuously moving elastic band in a stretched condition;
    (b) superposing said elastic band on a continuously moving support tape having a sufficiently high flexibility not to hinder a given expansion and contraction ability of said elastic band and a width larger than that of said elastic band and then nipping such assembly between a first pair of nip rollers to form a combined elastic band;
    (c) continuously feeding said combined elastic band onto a surface of a rotary suction drum and severing said combined elastic band by a cutter adapted to be opposed to the surface of said suction drum when the latter has rotated by a predetermined angle;
    (d) intermittently feeding said combined elastic band which has been severed and isolated on the surface of said suction drum into the predetermined lengths onto each side and longitudinally of the web being continuously fed around a second nip roller placed to be opposed to said suction drum so as to form the interconnected articles; and
    (e) severing said web transversely of said web in the areas defined between the longitudinal ends of the respectively adjacent lengths of the severed combined elastic band attached to said web to form the individual articles.

2. Method for attaching elastic band to sanitary articles according to claim 1, wherein, wherein said suction drum has a circumferential velocity higher than a velocity at which said combined elastic band is fed from said first nip rollers and including a stationary suction area and a stationary non-suction area so that said combined elastic band is fed onto the surface of said stationary suction area and said combined elastic band thus fed is cut by said cutter placed to be opposed to said surface of the stationary suction area every time said suction drum has rotated by a predetermined angle; wherein said severed and isolated length of combined elastic band travels while fixedly held on the surface of said stationary suction area under a suction of this area and a new leading end of said combined elastic band to be subsequently cut travels while held on the surface of said stationary suction area but with a slippage occurring against said suction effect, as said suction drum further rotates, so that the trailing end of said severed and isolated length of combined elastic band is spaced from said new leading end of the combined elastic band to be subsequently cut by a predetermined distance; and wherein said severed and isolated length of combined elastic band travels to said stationary non-suction area in which said severed and isolated length of combined elastic band leaves the surface of said suction drum and is then fed to said web at the interval corresponding to said predetermined distance with respect to a following length of combined elastic band.

3. Method for attaching elastic band to sanitary articles according to claim 1, wherein said suction drum has a circumferential velocity exactly corresponding to a velocity at which said combined elastic band is fed from said first pair of nip rollers and includes a stationary suction area, a first stationary non-suction area and a second stationary non-suction area located within said stationary suction area so that said combined elastic band is fed onto the surface of said stationary suction area extending across said second stationary non-suction area, then cut by the cutter placed to be opposed to the surface of said second non-suction area every time said suction drum has rotated by a predetermined angle and the trailing end of a length thus cut and isolated from said combined elastic band and a new leading end of combined elastic band to be subsequently cut contract so as to be spaced from each other by a predetermined distance; and wherein said length cut and isolated from the combined elastic band tranvels to said first stationary non-suction area in which said isolated length of combined elastic band leaves the surface of said suction drum, and then fed onto said web at the interval corresponding to said predetermined distance with respect to a following length of combined elastic band.

4. Method for attaching elastic band to sanitary articles according to claim 1, wherein the surface of said first pair of nip rollers destined to be brought in contact with adhesive applied on said elastic band is coated with film of mold release agent to prevent said adhesive from clinging to said surface.

5. Method for attaching elastic band to sanitary articles according to claim 1, wherein said combined elastic band is fed onto the surface of said suction drum so that said elastic band is not brought in contact with said surface or said elastic band is faced outwards.

6. Method for attaching elastic band to sanitary articles according to claim 1, wherein a plurality of rubber strands having a unit cross-section of 0.03 to 0.6 mm$^2$ and a total cross-section of 0.12 to 2.7 mm$^2$ serving as said elastic band and prestretched by 100 to 400% are placed on said support tape at predetermined intervals transversely of said support tape.

7. Method for attaching elastic band to sanitary articles according to claim 1, wherein said support tape is 10 to 70 mm wide and made of plastic film or nonwoven fabric.

8. Method for attaching an elastic band, in a stretched condition, to a continuously moving web forming interconnected diapers on each side thereof longitudinally at predetermined intervals, said method comprising steps of:
   (a) continuously or intermittently applying adhesive on the continuously moving elastic band in a stretched condition;
   (b) superposing said elastic band in said stretched condition on a continuously moving support tape having a sufficiently high flexibility not to hinder a given expansion and contraction ability of said elastic band and a width larger than that of said elastic band and then nipping such assembly between a first pair of nip rollers to form a combined elastic band;
   (c) continuously feeding said combined elastic band onto a surface of a rotary suction drum and severing said combined elastic band by a cutter placed to be opposed to the surface of said suction drum when the latter has rotated by a predetermined angle;
   (d) intermittently feeding said combined elastic band which has been severed and isolated on the surface of said suction drum into the predetermined lengths onto each side and longitudinally of a first web being continuously fed around a second nip roller placed to be opposed to said suction drum so as to form the interconnected diapers;
   (e) feeding said first web and a second web;
   (f) feeding respective absorbent cores which have been prefabricated between said first web and said second web at predetermined intervals to form interconnected diapers comprising these first and second webs and absorbent cores integrally bonded together; and
   (g) severing said first and second webs transversely in areas defined between respectively opposed ends of said severed and isolated lengths of combined elastic band which have been attached to said first web to for individual diapers.

9. Method for attaching elastic band to disposable diapers according to claim 8, wherein one of said first and second webs is water-impervious backsheet and the other of said first and second webs is water-pervious topsheet.

* * * * *